United States Patent [19]
Ringot et al.

[11] Patent Number: 5,279,337
[45] Date of Patent: Jan. 18, 1994

[54] PROCESS AND INSTALLATION FOR TRANSFERRING OUT OF A TIGHT ENCLOSURE A FLUID CONTAINED IN A SEALED CONTAINER

[75] Inventors: Gilbert Ringot, Querqueville; Denis Ferron, Equeurdreville, both of France

[73] Assignee: Cogema Compagnie Generale Des Matieres Nucleaires, France

[21] Appl. No.: 909,592

[22] Filed: Jul. 7, 1992

[30] Foreign Application Priority Data

Jul. 10, 1991 [FR] France ............................... 91 08686

[51] Int. Cl.$^5$ ............................................. G01N 1/10
[52] U.S. Cl. .......................................... 141/1; 73/863; 73/864.86; 73/864.74; 141/329; 141/97; 141/85; 141/250
[58] Field of Search ..................... 141/1, 329, 330, 130, 141/85, 97, 168, 250, 284; 73/864.79, 864.91, 864.86, 864.85, 864, 863

[56] References Cited

U.S. PATENT DOCUMENTS

| | | | |
|---|---|---|---|
| 3,026,730 | 3/1962 | Howarth et al. | 141/329 |
| 3,383,923 | 5/1968 | Conche et al. | 141/329 X |
| 4,078,895 | 3/1978 | Moran | 141/130 X |
| 4,170,798 | 10/1979 | Krumdieck | 141/329 |
| 4,662,231 | 5/1987 | Schaarschmidt et al. | 73/863 |
| 4,665,758 | 5/1987 | Schaarschmidt | 73/863.32 |
| 4,939,940 | 10/1990 | Tsukida | 73/864.74 |
| 5,060,704 | 10/1991 | Rohrbough | 141/329 |

FOREIGN PATENT DOCUMENTS

| | | |
|---|---|---|
| 0078212 | 5/1983 | European Pat. Off. . |
| 3044424 | 6/1982 | Fed. Rep. of Germany . |
| 2041587 | 1/1971 | France . |
| 2058751 | 5/1971 | France . |
| 2515350 | 4/1983 | France . |

Primary Examiner—Ernest G. Cusick
Attorney, Agent, or Firm—Pearne, Gordon, McCoy & Granger

[57] ABSTRACT

A process and apparatus for the transfer out of a tight enclosure of a fluid solution contained in a polluted container (R1). The transfer is accomplished without removing the polluted container from the enclosure and without breaking the seal of the polluted container. After a clean container (R2) is placed in a receptacle (30) normally isolated from the remainder of the enclosure, the solution is transferred into the clean container (R2) vacuum by a needle. Transfer of the clean container out of the enclosure takes place pneumatically following rotation of a casing containing the receptacle.

10 Claims, 4 Drawing Sheets

PROCESS AND INSTALLATION FOR TRANSFERRING OUT OF A TIGHT ENCLOSURE A FLUID CONTAINED IN A SEALED CONTAINER

BACKGROUND OF THE INVENTION

The invention relates to a process for the transfer out of a tight enclosure of a fluid contained in a sealed container such as a jar sealed by a diaphragm, without removing the container from the enclosure and without breaking its seal. The invention also relates to an installation for performing this process.

In irradiated nuclear fuel processing plants, it is a standard practice to carry out at different points of the process sampling operations on the active solutions with a view to analyzing and measuring the said samples.

As described in FR-A-2 515 350, the sampling operations can, in particular, be performed in plastic jars, which are placed in containers known as sliders, whose special shape aids the transfer of the jars in tubes, under the action of pneumatic transfer means. Each jar is sealed by a perforatable diaphragm.

When the analysis chain belongs to a shielded chain within which takes place the removal of the samples, the jars containing the latter can be directly transferred into said analysis chain by the aforementioned pneumatic transfer means and without special precautions being taken.

However, when certain measurements or analyses are performed outside the shielded chain containing the samples, as could in particular be the case for certain radiometry operations or certain physical measurements concerning weakly active solutions, the transfer of the samples out of the shielded chain comes up against certain difficulties, particularly when the measurements to be performed require the transfer to take place without any dilution of the sample taken.

In particular, it is essential that the transfer of samples out of the shielded chain takes place under clean conditions, which is not the case with jars containing samples received within the shielded chain, bearing in mind the pollution existing in the latter. Moreover, the transfer of samples to the exterior of the shielded chain must be performable without polluting the samples and without the new clean environment receiving them being contaminated during transfer. It must also be possible to check that the samples in their new clean environment are not of an excessively irradiating nature, if it is wished to carry out the analyses without using glove boxes.

SUMMARY OF THE INVENTION

The invention specifically relates to a process and an installation making it possible to transfer out of a tight enclosure into a new clean environment fluid samples initially contained in polluted containers, without removing the latter from the enclosure and without breaking the seal thereof.

According to the invention this result is achieved by means of a process for transferring out of a tight enclosure a fluid contained in a first container, without removing the latter from the enclosure and without breaking the seal of the latter, comprising introducing a second container under vacuum into a mobile receptacle placed within the enclosure, by a tube tightly traversing a wall of the enclosure and issuing into the receptacle when the latter occupies a first position, placing the mobile receptacle in a second position, in which a perforatable zone of the second container is exposed to the interior of the enclosure and perforating said zone, as well as a perforatable zone of the first container by means of the two ends of the same needle, so as to carry out an automatic transfer of the fluid into the second container under vacuum and then bringing the mobile container into its first position and evacuating the second container out of the enclosure by the said tube.

Advantageously, the second container is introduced into the mobile receptacle and the second container is discharged from the enclosure by pneumatic transfer means.

The invention also relates to an installation for the transfer out of a tight enclosure of a fluid contained in a first container, without removing the latter from the enclosure and without breaking the seal of the latter, comprising a receptacle mobile within a body placed in the enclosure between a first position and a second position, a tube tightly traversing a wall of the enclosure and connected to the body, so as to issue into the receptacle when the latter occupies its first position for introducing into it a second container under vacuum, a hole formed in the body at a location facing the receptacle, when the latter occupies its second position and a needle holder carrying a needle, whereof a first end can be fixed in a perforatable zone of the first container and whereof a second end can be fixed in a perforatable zone of the second container, through the said hole, when the receptacle occupies its second position.

Preferably, the body housing the mobile receptacle supports, in front of the hole permitting the passage of the needle, a guiding member on which a slide, able to receive the needle holder, can move in a direction coinciding with the axis of the hole.

In order to permit the discharge of the second container, when the fluid contained in the first container has been transferred into it, the installation advantageously has a pipe, which tightly traverses the container wall and has a first end connected to the body, so as to issue into the receptacle opposite to the tube and a second end connected to air introduction means located outside the enclosure.

The body housing the receptacle can also have an orifice for the exceptional discharge of the second container, which is normally sealed by a plug, it being possible to bring the receptacle in front of it when the latter is in a third position. A locking member installed in the body then normally prevents the passage of the receptacle into the third position when said locking member is not operated.

According to a preferred embodiment of the invention, the mobile receptacle is mounted in a rotary shell or casing, whose axis is perpendicular to the axis of the receptacle.

BRIEF DESCRIPTION OF THE DRAWING FIGURES

The invention is described in greater detail hereinafter relative to a non-limitative embodiment and with reference to the attached drawings, wherein show:

FIG. 1 A side view, in part section, diagrammatically illustrating a transfer installation according to the invention.

FIG. 2 A side view, in vertical section, illustrating on a larger scale that part of the installation located within the tight enclosure.

FIG. 3 A larger scale sectional view along line III—III of FIG. 2.

FIG. 4 A vertical sectional view comparable to FIG. 2, illustrating on an even larger scale the stage of transferring fluid between the two containers.

DETAILED DESCRIPTION OF THE PREFERRED EMBODIMENT

Figure 1:
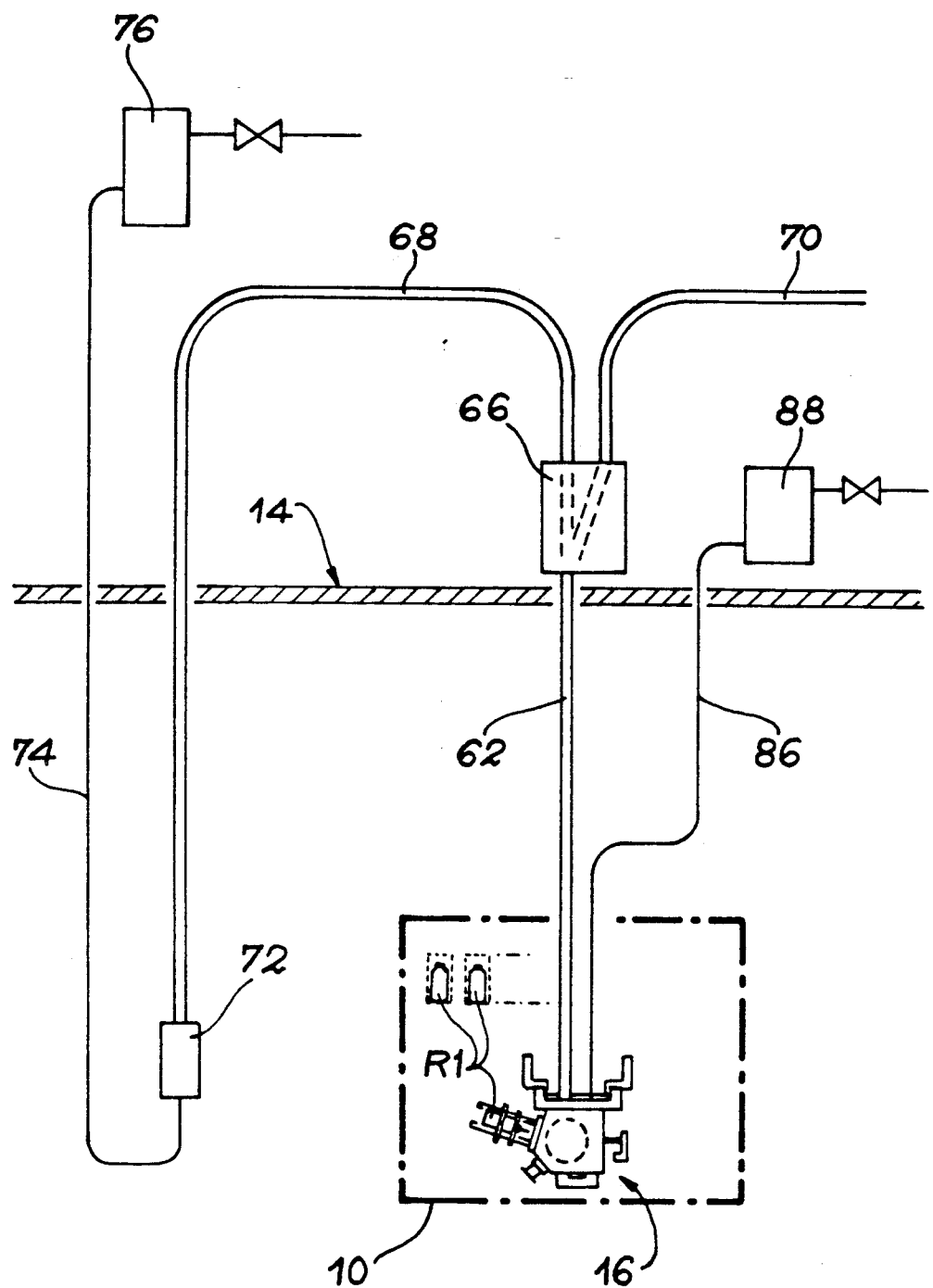

In FIG. 1, the reference numeral 10 designates a tight enclosure, e.g. belonging to a shielded chain, in which takes place analyses on irradiated nuclear fuel solutions. Within the enclosure are provided several containers R1, such as plastic jugs or jars, into which have previously been introduced samples of weakly active solutions taken from different points within the plant. For illustration purposes, these samples may have taken place within sampling units of the type described in FR-A-2 515 350. Each of the jars constituting the containers R1 is sealed at one of its ends by a perforatable diaphragm and placed in a cylindrical slider permitting its pneumatic transfer to the shielded chain. The tight enclosure 10 is placed in a confinement cell 14, whereof only the upper wall can be seen in FIG. 1.

According to the invention, an installation is provided for transferring out of the tight enclosure 10 and the cell 14 containing it, each of the fluid samples contained in the polluted containers R1, without removing the latter from the enclosure 10 and without breaking the seal of the latter. This transfer can serve the purpose of bringing the fluid samples contained in each of the containers R1 into not shown glove boxes located outside the cell 14 and in particular for carrying out radiometric analyses or physical measurements.

This installation is designed for successively carrying out the transfer of each of the fluid samples contained in the polluted containers R1 into unpolluted, new containers R2 (FIG. 2), which can be identical to the polluted containers, within the actual tight enclosure 10, followed by the transfer of said unpolluted, new containers outside the tight enclosure 10 and then the cell 14.

For carrying out the transfer between the containers R1 and R2, the installation mainly comprises an inter-container transfer apparatus located within the tight enclosure 10 and designated in general by the reference numeral 16 in FIG. 1. This inter-container transfer apparatus 16 will now be described in greater detail relative to FIGS. 2 and 3.

The inter-container transfer apparatus 16 placed within the tight enclosure 10 comprises a body 18, e.g. made from a rigid plastics material. This body 18 has a recess 20, which has a circular vertical cross-section, which issues laterally on one side in the manner illustrated in FIG. 3. This recess 20 houses a rotary casing 22, e.g. made from a transparent plastics material and which is able to rotate within the recess 20 about the horizontal axis of the latter.

To permit the control of the rotation of the casing 22 within the recess 20, a remotely manipulatable handle 24 is fixed to the face of the casing 22 turned towards the open end of the recess 20, e.g. by screws 26. These screws are also used for fixing to the corresponding face of the casing 22 an annular sealing cup 28, which tightly seals the recess 20 relative to the atmosphere contained in the tight enclosure 10.

The rotary casing 22 internally defines a cylindrical receptacle 30, whose axis is radially oriented relative to the axis of the casing 22. This receptacle 30 issues by one of its ends directly onto the peripheral surface of the casing 22, whereas it is extended at its opposite end by a coaxial cylindrical passage 32, which also issues onto the outer peripheral surface of the casing 22. The diameter of the receptacle 30 slightly exceeds the external diameter of the new containers R2, whereas the passage 32 has a smaller diameter.

Figure 2:
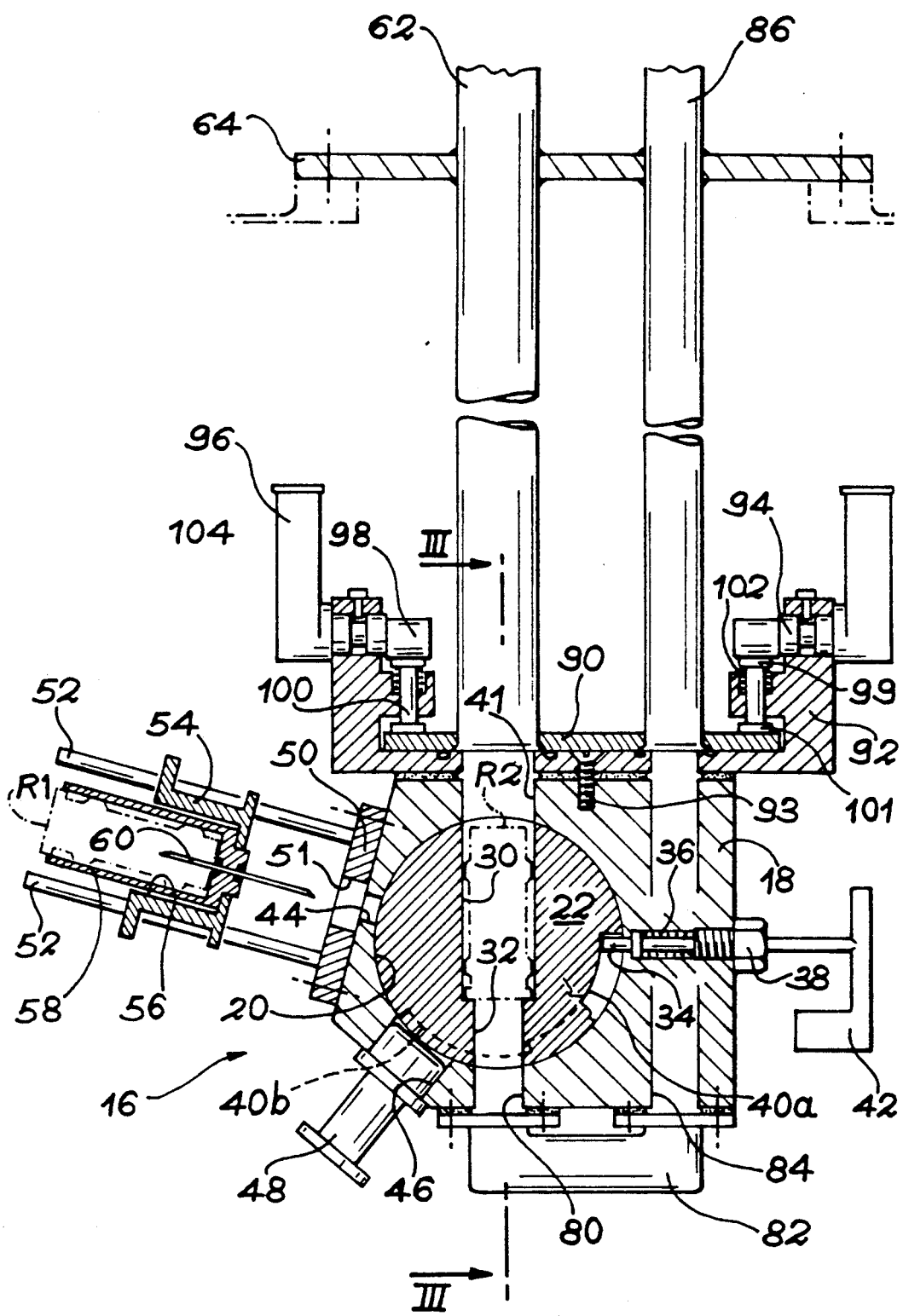

As is more particularly illustrated by FIG. 2, the rotary movement of the casing 22 about its axis is normally limited by a locking rod 34 slidingly received in a bore formed in the body 18, in a direction radially oriented with respect to the pivoting axis of the casing 22, said direction being horizontal in the embodiment shown. The locking rod 34 is moved radially towards the axis of the casing 22 by a compression spring 36, which bears on a guide screw 38 fixed to the body 18. In this way, the end of the locking rod 34 normally projects into a circular arc-shaped groove formed on the outer peripheral surface of the casing 22, said groove being centred on the axis of the latter.

The aforementioned groove has a relatively deep, main part 40a, in which is normally located the end of the locking rod 34. This main part 40a is extended by a less deep, complimentary part 40b, into which can be brought the corresponding end of the locking rod 34, when the latter is drawn radially towards the outside by means of a remotely manipulatable handle 42, integral with the end of the rod 34 located outside the body 18.

Figure 3:
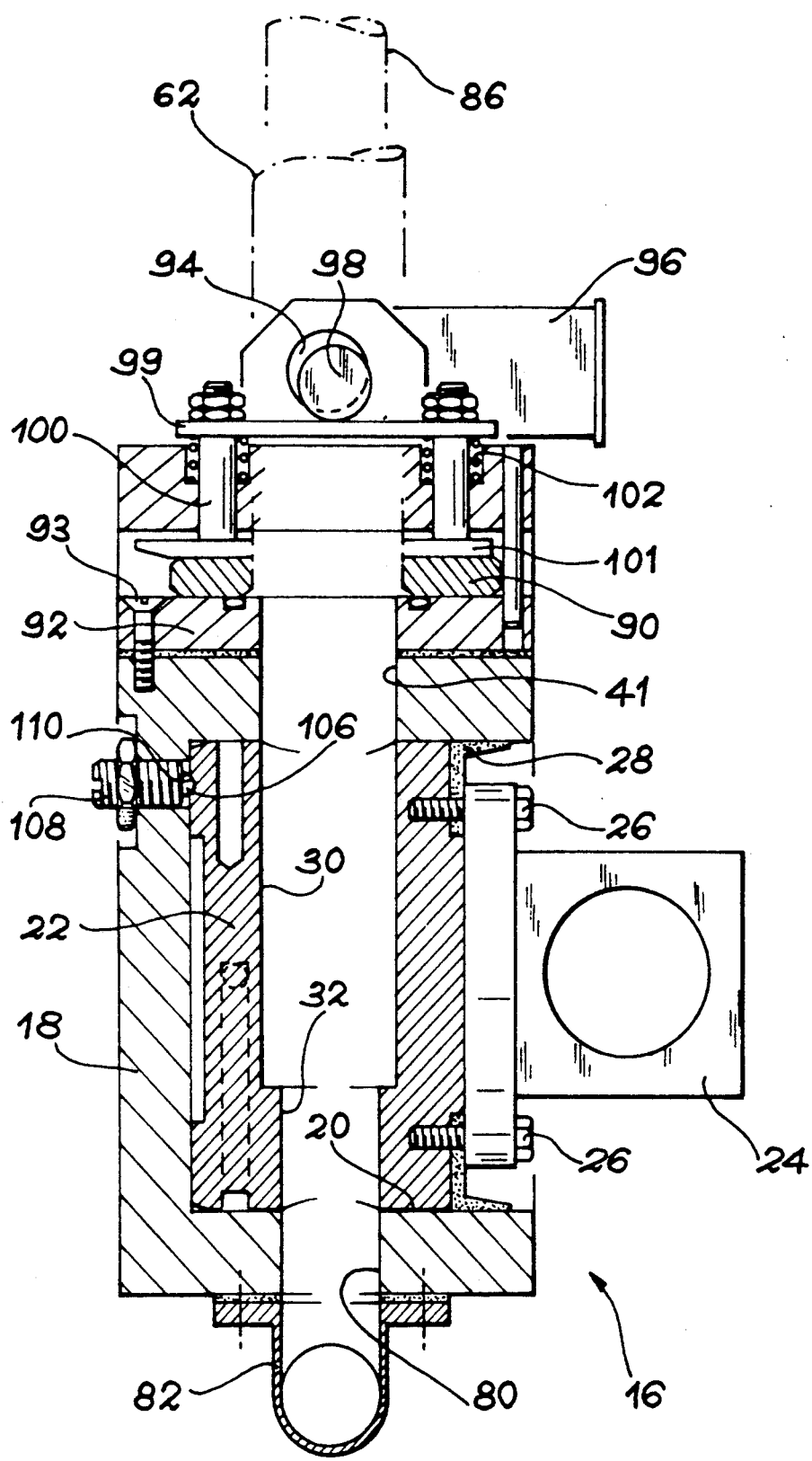
Figure 4:
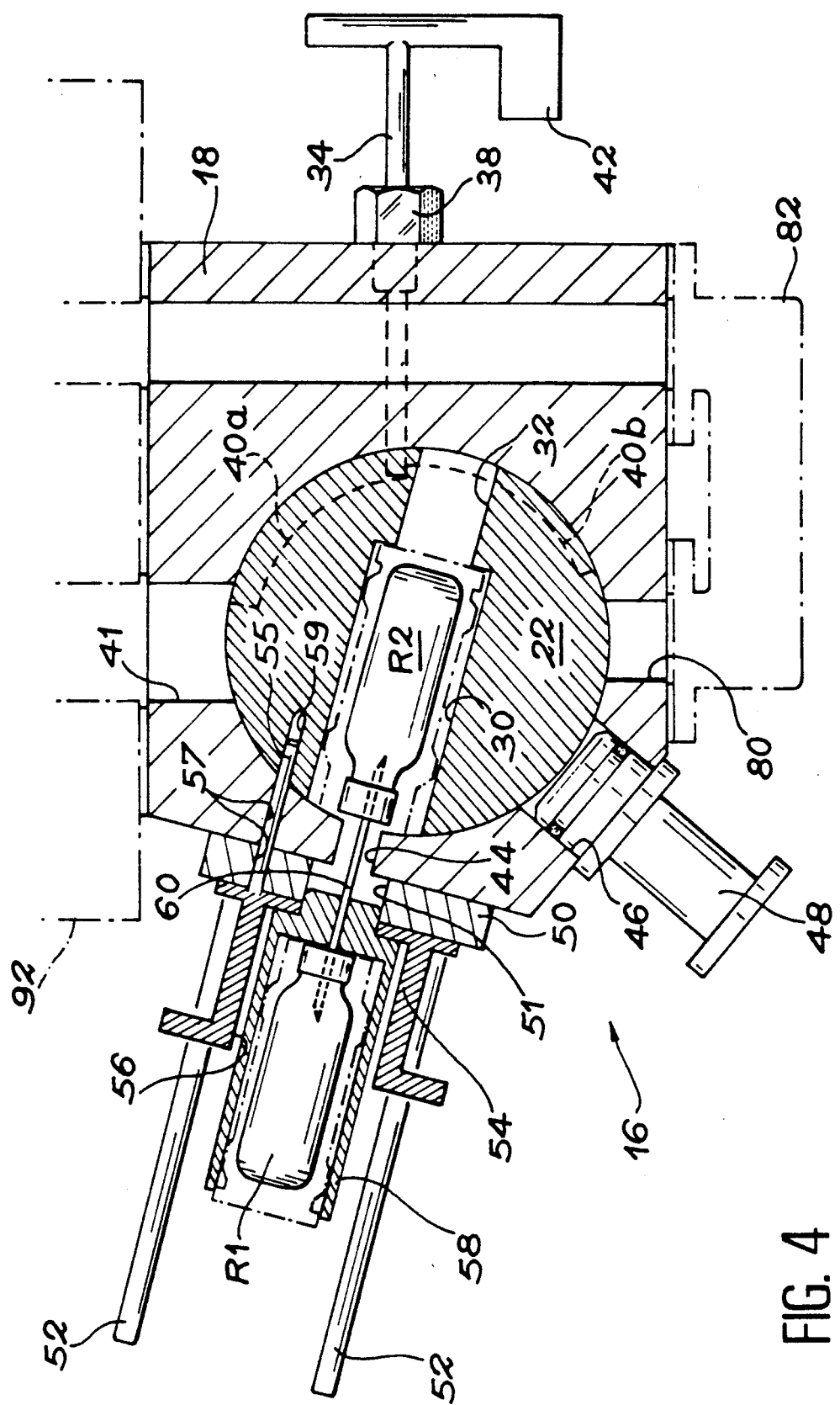

When the end of the locking rod 34 is positioned in the relatively deep main part 40a of the groove, the rotary casing 22 can be displaced between a first position, illustrated in FIGS. 2 and 3, and a second position, illustrated in FIG. 4. In the first position, the receptacle 30 is vertically oriented in such a way that its open end issues upwards in front of a passage 41 having the same diameter as the receptacle. In the second position of the casing 22, the receptacle is oriented in such a way that its open end issues in front of a through hole 44 having a small diameter and which is made in the body 18 in a direction oriented radially with respect to the recess 20. This second position can be displaced by an angle slightly smaller than 90° with respect to the first position.

When an operator draws the handle 42 of the locking rod 34 toward himself, while still continuing to act on the handle 24 in order to turn the casing 22 beyond the second aforementioned position, he makes the end of the rod 34 penetrate the complimentary part 40b of the groove. Thus, the operator can bring the receptacle 30 into a third position, in which the open end of the receptacle is positioned facing an exceptional discharge orifice 46 having the same diameter as the receptacle 30 and which is normally sealed by a remotely manipulatable plug 48. This exceptional discharge orifice 46 is located in the lower part of the body 18, so as to allow a discharge by gravity of a container R2 placed in the receptacle 30, in the case of the non-functioning of the pneumatic transfer system.

An indexing ball 106 (FIG. 3) carried by a screw 108 is mounted on the body 18 in the bottom of the recess 20, so as to be able to penetrate three spherical impressions 110 formed on the corresponding face of the casing 22, when the latter occupies one of the three aforementioned positions.

As is more particularly illustrated by FIG. 2, the inter-container transfer apparatus 16 also comprises a guide member fixed to a planar face of the body 18 and in which is formed the hole 44. This guide member comprises a plate 50, provided in its center with a hole 51 aligned with the hole 44 and whose diameter is slightly larger. The plate 50 is fixed to the body 18, e.g. by means of not shown screws (not shown). The plate 50 supports guide columns 52 oriented parallel to the axis of the hole 44. The guide columns 52 can receive a slide 54 able to move along the columns.

The slide 54 has on its face turned towards the body 18, a rod 55 which penetrates the aligned holes 57 formed in the plate 50 and in the body 18, as well as in a hole 59 formed in the casing 22, when the latter is in its second position (FIG. 4). The slide 54 internally defines a cylindrical slot 56 normally aligned with the hole 44 and into which can be introduced a needle holder 58. The latter has a tubular part centred on the axis of the hole 44 when it is received in the slot 56 and a bottom, which is to be turned towards the hole 44 and which is tightly traversed, in accordance with the axis of said hole, by a needle 60. The needle 60 is tapered at each of its ends, so as to be able to perforate diaphragms respectively sealing the polluted container R1 containing the fluid solution to be transferred and the clean container R2 into which said solution is to be transferred.

The tubular part of the needle holder 58 is dimensioned in such a way that the polluted container R1 containing the fluid solution to be transferred can be introduced into it with its diaphragm turned towards the needle 60. This introduction generally takes place before the needle holder 58 is introduced into the slot 56 of the slide 54. This operation is carried out remotely with the aid of appropriate handling means also equipping the tight enclosure 10. These handling means can in particular be remote manipulators or telemanipulators.

When the polluted container R1 containing the fluid solution to be transferred has been placed in the needle holder 58 in such a way that its diaphragm is perforated by the needle 60, the needle holder 58 is placed in a slot 56 of the slide 54, which is then kept remote from the plate 50. Then, in remote manner, the operator then controls the rotation of the casing 22, so as to bring the open end of the receptacle 30 in front of the hole 44. The clean container R2 introduced before-hand into the receptacle 30 is then disposed in such a way that its diaphragm faces the hole 44. The operator then moves the slide 54 in which is placed the needle holder 58 carrying the polluted container R1 towards the hole 44 until the slide 54 abuts against the plate 50. At this moment, the end of the needle 60 opposite to that fixed in the polluted container R1 has perforated the diaphragm of the clean container R2 placed in the receptacle 30, as illustrated in FIG. 4.

In view of the fact that the interior of the container R2 was previously placed under vacuum, a transfer of the fluid solution initially contained in the polluted container R1 to the clean container R2 then takes place automatically. When this transfer is at an end, operations which are the reverse of those described hereinbefore are carried out in remote manner by the operator, so as to discharge the polluted container R1 to a waste bin located within the tight enclosure 10 and transfer the clean container R2 then containing the fluid solution to the outside of said enclosure.

The introduction of a clean container R2 into the receptacle 30, as well as its transfer out of the enclosure 10 following the introduction into it of the fluid solution take place by a tube 62 (FIG. 3), whereof one part located towards the interior of the enclosure 10 is vertically oriented, so as to be connected by its lower end to the body 18, in the extension of the passage 41 overhanging the receptacle 30 when the latter occupies its first position. The internal diameters of the tube 62, the passage 41 and the receptacle 30 are identical and slightly in excess of the external diameter of the clean containers R2, so as to permit the displacement of the latter by compressed air injection.

Above the inter-container transfer apparatus 16, the tube 62 traverses a wall 64 of the tight enclosure 10, advantageously constituted by a dismantable part, as is diagrammatically illustrated in FIG. 2. On once again referring to FIG. 1, it can be seen that the tube 62 then traverses the upper partition of the confinement cell 14 and is connected above the latter to a switching device 66, which makes it possible to link the tube 62 either to a tube 68 for supplying new containers R2 under vacuum, or to a tube 70 for the transfer of a new container R2 containing a fluid solution.

The tube 68 then traverses the partition 14 of the cell again in order to issue at its opposite end in a casing 72 for the introduction of new containers under vacuum, opposite to an air supply pipe 74. The pipe 74 is supplied with air through a device 76 located outside the cell 14 and making it possible to interrupt the air supply and place the pipe 74 under atmospheric pressure.

The transfer of new vacuum containers from the introduction casing 72 into the receptacle 30 takes place by injecting air through the pipe 74 after placing the switching device 66 and the casing 22 in appropriate positions.

The transfer tube 70 is linked by its end opposite to the switching device 66 to a not shown glove box, in which different physical measurements or radiometric analysis can be performed on fluid samples contained in the containers R2.

In order to transfer each of the new containers R2 out of the tight enclosure 10 after a fluid sample has been transferred into the container, use is made of an air injection into the receptacle 30, which takes place through the passage 32, opposite to the open end of the receptacle. This passage 32 links the bottom of the receptacle 30 with a passage 80 formed in the body 18, when the casing 22 occupies its first position. This passage 80 is axially aligned with the passage 41 formed in the body 18, in the extension of the tube 62. A tube 82 tightly fixed to the body 18 links the passage 80 with a second vertical passage 84 formed in the body 18 and traversing the entire length of the latter. To the upper end of the passage 84 is tightly connected a pipe 86, which extends vertically within the tight enclosure 10, parallel to and alongside that part of the tube 62 located in said enclosure.

The pipe 86 tightly traverses the enclosure wall 64, as well as the wall of the cell 14 (FIG. 1) for connection at its opposite end with an air source by means of a device 88 making it possible to interrupt the air supply and place the pipe 86 under atmospheric pressure.

When the air is introduced by the pipe 86, the container R2 in the receptacle 30 is automatically transferred by the tube 62 and then the tube 70 to the glove box into which the latter issues, when the switching device 66 is placed in its appropriate position.

In the embodiment illustrated in the drawings, the inter-container transfer device 16 is tightly fixed to a horizontal plate 90 (FIG. 2), to which are welded the lower ends of the tube 62 and the pipe 86.

For this purpose, a slide bar 92 is tightly fixed, e.g. by screws 93, to the upper horizontal face of the body 18. This slide bar 92 is attached, by a horizontal sliding movement in a direction perpendicular to the plane of FIG. 2, to the plate 90. Horizontally axed, rotary cams 94 are mounted in the slide bar 92, so as to be remotely manipulatable by levers 96. Each of the cams 94 carries at its end a roller 98, which bears on a horizontal bar or strip 99, connected by two rods 100 to a horizontal support block 101. The rods 100 are able to slide in a vertical direction in the slide bar 92. Each of the support blocks 101 can consequently bear against the upper face of the plate 90 in order to lock the latter against the slide bar in the appropriate position of the cams 94. A spring 102 associated with each of the rods 100 moves the latter upwards in order to normally move the blocks 101 away from the plate 90. Each of the cams 94 can be locked by a screw 104.

Obviously, the invention is not limited to the embodiment described in exemplified manner hereinbefore and covers all variants thereof. Thus, the rotary casing carrying the receptacle can be replaced by a sliding valve.

We claim:

1. Process for transferring, out of an enclosure having a wall, a fluid contained in a first container having a perforatable zone, without removing said first container from the enclosure and without breaking a seal of the first container, comprising:
   introducing a second container into a mobile receptacle placed within the enclosure, by a tube traversing the wall of the enclosure and issuing into the receptacle when the receptacle occupies a first position, said second container being under vacuum and having a perforatable zone,
   placing the mobile receptacle in a second position in which the perforatable zone of the second container is exposed to an interior of the enclosure, and perforating said zone by means of a first end of a needle, as well as a perforatable zone of the first container, by means of a second end of the needle, so as to carry out an automatic transfer of the fluid from said first container into the second container under vacuum, and then,
   bringing the mobile receptacle into the first position and evacuating the second container out of the enclosure by the said tube.

2. Process according to claim 1, wherein the second container is introduced into the mobile receptacle and the second container is discharged out of the enclosure by pneumatic transfer means.

3. Installation for the transfer, out of an enclosure having a wall, of a fluid contained in a first container having a perforatable zone, without removing said first container from the enclosure and without breaking a seal of the first container, comprising:
   a body placed in the enclosure,
   a receptacle mobile within said body between a first position and a second position,
   a tube traversing the wall of the enclosure and connected to the body so as to issue into the receptacle when the receptacle occupies the first position for introducing into the receptacle a second container, said second container having a perforatable zone and being under vacuum,
   a hole formed in the body at a location facing the receptacle when the receptacle occupies the second position and,
   a needle holder carrying a needle, whereof a first end of the needle can be fixed in the perforatable zone of the first container and whereof a second end of the needle can be fixed in the perforatable zone of the second container, through the said hole, when the receptacle occupies the second position.

4. Installation according to claim 3, wherein a guide member is supported by the body, in front of the hole, and a slide, able to receive the needle holder, can travel on said guide member in a direction coinciding with the axis of said hole.

5. Installation according to claim 3, wherein air introduction means are provided outside the enclosure, and a pipe traversing the wall of the enclosure has a first end connected to the body so as to issue into the receptacle opposite to the tube when the receptacle occupies the first position, and a second end connected to said air introduction means outside the enclosure.

6. Installation according to claim 5, wherein the tube and the pipe have two first parallel parts traversing the enclosure wall and two parts at least partly formed in the body, dismantable connecting means being provided to fix the body to the first parallel parts.

7. Installation according to claim 3, wherein the body has an exceptional discharge orifice for the second container in front of which can be brought the receptacle in a third position, a plug normally sealing said exceptional discharge orifice.

8. Installation according to claim 7, wherein a locking member mounted in the body normally prevents passage of the receptacle into the third position.

9. Installation according to claim 3, wherein a rotary casing, whose axis is perpendicular to the receptacle axis, is provided with said mobile receptacle.

10. Installation according to claim 3, wherein indexing means are mounted in the said body in order to index each of the positions.

* * * * *